US009802980B2

United States Patent
Taran et al.

(10) Patent No.: US 9,802,980 B2
(45) Date of Patent: Oct. 31, 2017

(54) METHOD FOR PRODUCING PYRAZOLES, NOVEL PYRAZOLES AND APPLICATIONS THEREOF

(71) Applicant: COMMISSARIAT A L'ENERGIE ATOMIQUE ET AUX ENERGIES ALTERNATIVES, Paris (FR)

(72) Inventors: Frederic Taran, Gif sur Yvette (FR); Manon Chaumontet, Issy les Moulineaux (FR); Sergii Kolodych, Orsay (FR); Evelia Rasolofonjatovo Andovola, Massy (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 28 days.

(21) Appl. No.: 14/766,048

(22) PCT Filed: Feb. 7, 2014

(86) PCT No.: PCT/FR2014/050239
§ 371 (c)(1),
(2) Date: Aug. 5, 2015

(87) PCT Pub. No.: WO2014/122407
PCT Pub. Date: Aug. 14, 2014

(65) Prior Publication Data
US 2015/0368295 A1      Dec. 24, 2015

(30) Foreign Application Priority Data
Feb. 11, 2013 (FR) ..................... 13 51146

(51) Int. Cl.
| | |
|---|---|
| C07K 5/08 | (2006.01) |
| C07H 19/06 | (2006.01) |
| C07D 401/04 | (2006.01) |
| C07D 409/04 | (2006.01) |
| C07D 231/12 | (2006.01) |
| C07D 403/12 | (2006.01) |
| C07D 401/12 | (2006.01) |
| C07H 15/26 | (2006.01) |
| C07H 19/073 | (2006.01) |
| C07D 405/14 | (2006.01) |
| C07D 405/12 | (2006.01) |
| C07H 1/00 | (2006.01) |
| C07H 13/04 | (2006.01) |

(52) U.S. Cl.
CPC ............. C07K 5/08 (2013.01); C07D 231/12 (2013.01); C07D 401/04 (2013.01); C07D 401/12 (2013.01); C07D 403/12 (2013.01); C07D 405/12 (2013.01); C07D 405/14 (2013.01); C07D 409/04 (2013.01); C07H 1/00 (2013.01); C07H 13/04 (2013.01); C07H 15/26 (2013.01); C07H 19/06 (2013.01); C07H 19/073 (2013.01)

(58) Field of Classification Search
None
See application file for complete search history.

(56) References Cited

U.S. PATENT DOCUMENTS

| | | |
|---|---|---|
| 3,063,978 A | 11/1962 | Lynn |
| 3,254,093 A | 5/1966 | Huisgen et al. |

OTHER PUBLICATIONS

Browne, D.L., et al., "A Sydnone Cycloaddition Route to Pyrazole Boronic Esters," Angew. Chem. Int. Ed., 2007, 46:8656-8658.
Browne, D.L., et al., "Investigation of the Scope and Regiochemistry of Alkynylboronate Cycloadditions with Sydnones," J. Am. Chem. Soc., Jun. 10, 2009, 131(22):7762-7769.
Camerano, J.A., et al., "Tris(pryazolyl)borate carbosilane dendrimers and metallodendrimers," Dalton Transactions, Jan. 2006, 44:5287.
Fang, Y., et al., "Synthesis of 2H-Indazoles by the [3+2] Dipolar Cycloaddition of Sydnones with Arynes," J. Org. Chem. 2011, 76(21):8840-8851.
Fustero, S., "From 2000 to Mid-2010: A Fruitful Decade for the Synthesis of Pyrazoles," Chem. Rev., 2011, 111(11):6984-7034.
Harju, K., et al., "Solid-Phase Synthesis of Amino Acid Derived N-Unsubstituted Pyrazoles via Sydnones," Org. Lett., 2009, 11(10):2219-2221.

(Continued)

Primary Examiner — Kamal Saeed
(74) Attorney, Agent, or Firm — Frost Brown Todd LLC

(57) ABSTRACT

A method for preparing a pyrazole of formula (I) in which R, R' and R" have different meanings, characterised in that it involves reacting a sydnone of formula (II) in which R and R' have the meanings already indicated, with an alkyne of formula (III) in which R" has the meaning already indicated, in the presence of copper, to obtain a pyrazole compound of formula (I) that is then isolated and salified if desired.

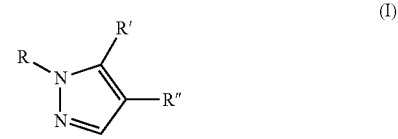

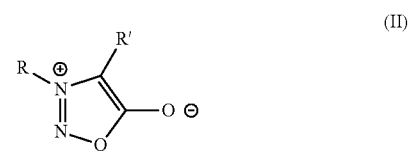

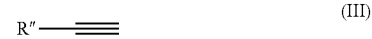

6 Claims, No Drawings

(56) References Cited

OTHER PUBLICATIONS

Hwang, J.Y., et al., "Solid-Phase Syntesis of 5-Amino-1-(Substituted Thiocarbamoy) payrazole and 1,2,4-Triazole Derivatives via Dithiocarbazate Linker," J. Comb. Chem., Jan. 2005, 7(1):136-141.
Padalkar, V.S., et al., "Synthesis and characterization of novel 2,2'-bipyrimidine fluorescent derivative for protein binding," Chem. Centeral J., Biomed Central, Ltd., LO, Nov. 9, 2011, 5(1):1-7.
Wu, C., "Pd-catalyzed oxidative coupling of monosubstituted sydnones and terminal alkynes," Tetrahedron Letters, Jul. 2011, 52(29):3797-3801.
Wu, C., et al., "Synthesis of 2H-Indazoles by the [3+2] Cycloaddition of Aryes and Sydnones," Org. Lett. 2010, 12(10):2234-2237.
International Search Report and Written Opinion dated Sep. 17, 2014 for Application No. PCT/FR2014-050239, 41 pgs.

METHOD FOR PRODUCING PYRAZOLES, NOVEL PYRAZOLES AND APPLICATIONS THEREOF

The present invention relates to a process for producing pyrazoles, novel pyrazoles impossible to produce to date, and applications thereof.

There are many processes for forming pyrazoles. Two main solutions can be retained as described in the recent review by Antonio Simon-Fuentes, Chem. Rev. 2011, 111, 6984-7034.

A first solution consists in using cyclo-condensation of 1,3-dielectrophiles, such as beta-diketones, with hydrazines. This solution has been known for many years and is probably still the most widely used to date for the synthesis of pyrazoles. However, this method has a certain number of limitations. In particular, it cannot be applied to all substrates; in particular hydrazine substrates having nucleophilic groups, such as amines, cannot be used. Likewise, dielectrophilic substrates which have other electrophilic centers, such as aldehydes, ketones or Michael acceptors, are to be eliminated. Furthermore, most of the time, the reaction conditions require the use of acids and/or high temperatures.

The second solution consists in preparing pyrazoles by 1,3-dipolar cycloaddition using alkynes and dipoles such as diazo-alkanes, nitrilimines or sydnones. The reaction with diazo-alkanes and nitrilimines requires strong-base conditions and the use of organic solvents, which is a considerable drawback when substrates that are fragile and/or only soluble in aqueous medium must be used. Furthermore, these reactions generate two regioisomers that have to be separated.

The reaction with sydnones is described in the literature according to two solutions.

A first solution consists in preparing the pyrazoles thermally. Thermal sydnone/alkyne cycloaddition has been known for many years and it has been described in particular by Kirsi Harju, Johanna Vesterinen, and Jari Yli-Kauhaluoma, Org. Lett. 2009, 10, 2219-2221 and by Duncan L. Browne, Matthew D. Helm, Andrew Plant, and Joseph P. A. Harrity, Angew. Chem. Int. Ed. 2007, 46, 8656-8658. The temperatures required for the reaction are conventionally above 120° C.

Another solution, described for example by Chunrui Wu, Yuesi Fang, Richard C. Larock and Feng Shi, Org. Lett. 2010, 10, 2234-2237 or by Yuesi Fang, Chunrui Wu, Richard C. Larock and Feng Shi, J. Org. Chem. 2011, 76, 8840-8851, consists in preparing pyrazoles from highly reactive alkynes. The sydnone/alkyne cycloaddition can then be carried out at ambient temperature when aromatic compounds called arynes, having an extremely reactive triple bond, are used. Arynes are not stable and must be prepared in situ from appropriate precursors.

Each of these solutions comprises significant drawbacks. The drawbacks of the first solution are linked to the drastic preparation conditions. The high temperatures, typically of about 150° C., are incompatible with numerous fragile substrates. The thermal reaction does not tolerate the presence of numerous reactive groups. Furthermore, two regioisomer products are formed, which reduces the synthesis yields and implies fastidious purifications.

The second solution uses very specific alkynes. It is therefore by nature limited in terms of the diversity of substrates that can be used. Only pyrazoles called 2H-indazoles can be synthesized by this reaction.

It would therefore be desirable to have a process which allows the production of an entire variety of pyrazoles, in particular comprising fragile or reactive groups. It would also be desirable for this process to be as general as possible and compatible with complex molecules and biological media.

Moreover, in order to increase the reaction yield, it would be desirable for this process to be regioselective and chemoselective.

Chunrui Wu also describes, in Tetrahedron Letters, vol. 52, No. 29, July 2011, the palladium-catalyzed oxidative coupling between monosubstituted sydnones and alkynes in toluene at 75° C. In certain reactions, a cupric salt combined with a silver-based compound is used to regenerate the palladium II. Seeking to prepare acetylenated compounds, the author accidentally obtained a pyrazole substituted with a pyridyl.

After lengthy research, the inventors have developed a process for producing pyrazoles, which makes it possible in particular to prepare novel pyrazoles impossible to produce up to now.

These pyrazoles correspond to formula I,

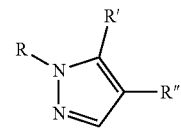

and have virtually no limitation with regard to the nature of the substituents R and R'' which can be of very great variety, ranging from a simple alkyl to proteins, as will be seen hereinafter in the examples.

Consequently, a subject of the present application is a process for preparing a pyrazole of formula I

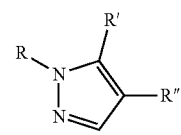

in which

R represents a hydrogen atom, a halogen atom, a thio or -thioalkyl group, a hydroxyl or alkoxy group, an amino or -aminoalkyl group, an alkyl radical containing from 1 to 8 carbon atoms which is unsubstituted or substituted one or more times with F, Cl, Br, I, CN, OH, $NH_2$, NH—($C_1$-$C_8$ alkyl), N—($C_1$-$C_8$ alkyl)$_2$, SH, an aryl radical containing 6 to 10 carbon atoms which is unsubstituted or substituted one or more times with an alkyl or alkoxy radical containing 1 to 8 carbon atoms, a heterocycle, an amino acid, a polypeptide, a protein, a nucleic acid, a DNA molecule, a polysaccharide, a polymer, a nanoparticle or a dendrimer;

R' represents a hydrogen atom, a halogen atom, a thio or -thioalkyl group, a hydroxyl or alkoxy group, an amino or -aminoalkyl group, an alkyl radical containing from 1 to 8 carbon atoms which is unsubstituted or substituted one or more times with F, Cl, Br, I, CN, OH, $NH_2$, NH—($C_1$-$C_8$ alkyl), N—($C_1$-$C_8$ alkyl)$_2$, SH, an aryl radical containing 6 to 10 carbon atoms which is unsubstituted or substituted one or more times with an alkyl or alkoxy radical containing 1 to 8 carbon atoms, a heterocycle;

R" represents a hydrogen atom, a halogen atom, a thio group, a hydroxyl group, an amino group, a hydrocarbon-based group or a hydrocarbon-based group containing from 1 to 100 heteroatoms, R" representing particularly a hydrogen atom, a halogen atom, a thio or -thioalkyl group, a hydroxyl or alkoxy group, an amino or -aminoalkyl group, an alkyl radical containing from 1 to 8 carbon atoms which is unsubstituted or substituted one or more times with F, Cl, Br, I, CN, OH, —O-heterocycle which is substituted or unsubstituted, $NH_2$, —NH—($C_1$-$C_8$ alkyl), —N—($C_1$-$C_8$ alkyl)$_2$, —NH—R''' or —($C_1$-$C_3$ alkyl)-NH—R''' where R''' represents a sulfonated group, SH, an aryl radical containing 6 to 10 carbon atoms which is unsubstituted or substituted one or more times with an alkyl or alkoxy radical containing 1 to 8 carbon atoms, a heterocycle, an amino acid, a polypeptide, a protein, a nucleic acid, a DNA molecule, a polysaccharide, a polymer, a nanoparticle or a dendrimer, characterized in that a sydnone of formula II

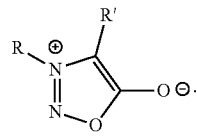

II in which R and R' have the meanings already indicated, is reacted with an alkyne of formula III

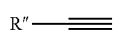

III in which R" has the meaning already indicated, in the presence of copper used as a catalyst metal, so as to obtain a pyrazole compound of formula I which is isolated and salified if desired.

The halogen atom may be a bromine or iodine atom, and preferably a chlorine atom.

The alkyl radical has a linear chain or branched chain and can contain from 1 to 8 carbon atoms and preferably from 1 to 5 carbon atoms. The appropriate alkyl groups comprise a methyl, an ethyl, a propyl, an isopropyl, a butyl, a sec-butyl and a tert-butyl. The same is true for the alkyl radical of the alkylthio, alkoxy or alkylamino group.

The term "aryl" denotes an aromatic carbocyclic radical containing 6 to 10 carbon atoms, unless otherwise indicated. The appropriate aryl groups comprise a phenyl, a naphthyl and a biphenyl. The substituted aryl groups comprise the aryl groups described above which are substituted one or more times, preferably once, with a halogen, an alkyl, a hydroxyl, an alkoxy, a nitro, a methylenedioxy, an ethylenedioxy, an amino, an alkylamino, a dialkylamino, a hydroxyalkyl, a hydroxyalkoxy or a carboxy.

The heterocycle may be a saturated, partially saturated or totally unsaturated heterocyclic group comprising one, two or three rings and a total number of from 5 to 10 ring atoms where at least one of the ring atoms is an N, O or S atom. Preferably, the heterocyclic group contains 1 to 3 ring heteroatoms chosen from N, O and S. The appropriate saturated and partially saturated heterocyclic groups comprise a tetrahydrofuranyl, a tetrahydrothienyl, a tetrahydropyranyl, a dihydropyranyl, a pyrrolidinyl, a piperidinyl, a piperazinyl, a morpholinyl, an oxoazolinyl, an isoxazolinyl, and the like. The appropriate heteroaryl groups comprise a furyl, a thienyl, a pyrrolyl, a pyrazolyl, an imidazolyl, a pyridyl, a pyrimidinyl, a benzopyranyl, an indolyl, a quinolinyl, an isoquinolinyl, a naphthyridinyl, and the like. Other examples of appropriate heterocyclic groups are a 2-quinolinyl, a 1,3-benzodioxyl, a 2-thienyl, a 2-benzofuranyl, a 2-benzothiophenyl, a 3-thienyl, a 2,3-dihydro-5-benzofuranyl, a 4-indoyl, a 4-pyridyl, a 3-quinolinyl, a 4-quinolinyl, a 1,4-benzodioxan-6-yl, a 3-indoyl, a 2-pyrrolyl, a benzopyran-6-yl, a 5-indolyl, a 1,5-benzoxepin-8-yl, a 3-pyridyl, a 6-coumarinyl, a 5-benzofuranyl, a 2-isoimidazol-4-yl, a 3-pyrazolyl, a 3-carbazolyl, a 2-thiazolyl, a 2-oxazolyl, a 1-imidazolyl and a 2-imidazolyl.

The heterocycle may be substituted at one or more substitutable sites with, for example, a halogen, an aryl, a $C_1$-$C_5$ alkyl, a hydroxyl, a $C_1$-$C_5$ alkoxy, a cyano, a trifluoromethyl, a nitro, an oxo, an amino, a $C_1$-$C_5$ alkylamino or a $C_1$-$C_5$ dialkylamino or even another heterocycle which can also be substituted itself.

The radicals which are substituted one or more times preferably contain 1 to 3 substituents.

A polypeptide may be, for example, angiotensin II, substance P, neurokine A, calcitoninin, oxytocin.

A protein may be, for example, an antibody, an enzyme, hemoglobin, transferrin, streptavidin.

A nucleic acid may be, for example, a molecule constituted of DNA or of RNA.

A polysaccharide may be, for example, chitosan, cellulose, alginates, dextran.

A polymer may be, for example, polyethylene glycol (PEG), polystyrene, polypropylene, polyethylene, polyacrylamide.

A nanoparticle may be chosen, for example, from quantum dots, carbon nanotubes, metal nanoparticles (Au, $Fe_3O_4$, $Cr_2O_3$, $Al_2O_3$, $BaFe_{12}O_{19}$).

A dendrimer may be chosen, for example, from PAMAM dendrimers and cyclotriphosphazene-PMMH.

When R''' represents a sulfonated group, it is preferably one of the sulfonated groups illustrated by the examples.

In the present application and in what follows, the expression "hydrocarbon-based group" denotes a linear, branched, cyclic or polycyclic hydrocarbon-based group, it being possible for these rings to be fused or not, containing from 1 to 100 heteroatoms, it being possible for these groups to be unsubstituted or substituted with one or more atoms or groups such as those cited for the definition of the radicals R' and R".

It should be noted that the sydnones of formula II are dipoles which exist in several tautomeric forms. Only one of the forms is represented above.

Under preferential conditions for carrying out the process described above, R represents an optionally substituted aryl or heteroaryl radical, in particular an optionally substituted aryl radical, particularly an optionally substituted phenyl radical, these various radicals and substituents having in particular the meanings indicated above.

Under other preferential conditions for carrying out the process described above, R' represents a hydrogen atom.

Under yet other preferential conditions for carrying out the process described above, R" represents a heteroaryl radical or an aryl radical or an alkyl radical containing from 1 to 8 carbon atoms, preferably one of the latter two.

Under most particularly preferred conditions, R and R', R' and R", R and R", and R, R' and R" have the preferred values indicated above.

The catalyst metal of the reaction is copper. Forms of copper that can be used in the process are for example and preferably either copper(I) salts such as CuI, CuOTf, CuCl, CuOAc, etc., and preferably CuI, or copper(II) salts such as CuSO$_4$, CuOTf$_2$, CuOAc$_2$, etc., and preferably CuSO$_4$, reduced in situ to Cu(I) salts using a reducing agent such as ascorbic acid, sodium bisulfite, zinc or copper metal, and preferably ascorbic acid.

The copper salts may either be used as they are, or preferably used in a form complexed with ligands, preferably nitrogenous ligands, for instance phenanthroline compounds such as IV below, triazole compounds such as V or VII below, pyridine compounds such as IX and X below, imidazole compounds such as VIII below, benzimidazole compounds such as VI below and phosphines, preferably nitrogenous ligands such as those mentioned above, particularly phenanthrolines. These nitrogenous ligands allow an increase in the catalytic activity of the copper, but also in the regioselectivity of the reaction, in particular in the case where R' is other than H.

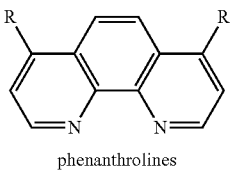

phenanthrolines

IV

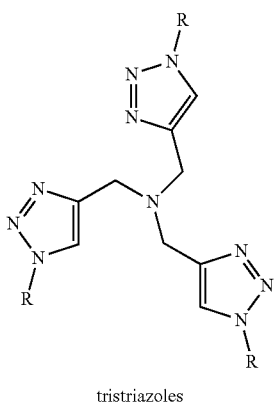

tristriazoles

V

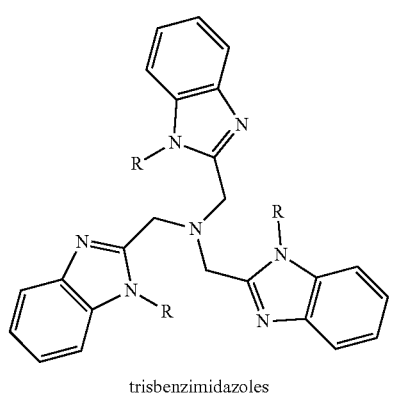

trisbenzimidazoles

VI

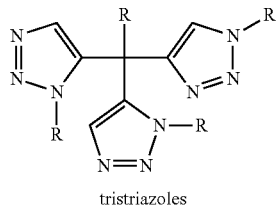

tristriazoles

VII

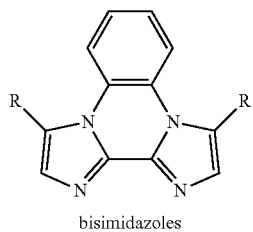

bisimidazoles

VIII

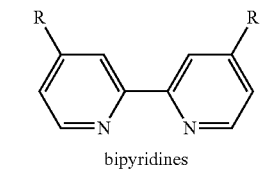

bipyridines

IX

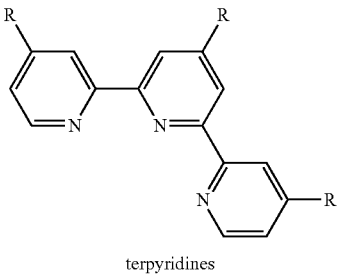

terpyridines

X

The above copper salts are preferably reduced in situ to salts which have a lower oxidation state.

The solvents that can be used for carrying out the present process may be organic solvents, water or organo-aqueous mixtures. It should be noted that, entirely notably, a physiological fluid, which is optionally complex, such as plasma or urine, cell lysates, or cell culture media can be used as solvent medium in the present invention, without disrupting the reaction.

The present process is not very sensitive to the pH of the reaction medium. However, it is preferred to carry out the process in a neutral medium, or particularly in an alkaline medium. For this purpose, use may be made, for example, of an organic base such as triethylamine or triethanolamine.

The reaction of a sydnone of formula II with an alkyne of formula III is preferably carried out at between 10° C. and 120° C., advantageously between 15° C. and 100° C., particularly between 15° C. and 70° C. For the preparation of sensitive or fragile pyrazole compounds of formula I such as a polypeptide, a protein, a nucleic acid, a DNA molecule, a polysaccharide, a nanoparticle or a dendrimer, the process is preferably carried out at between 15 and 50° C., advantageously between 20 and 40° C. When the pyrazole compound of formula I is not particularly sensitive or fragile, the process is preferably carried out at between 45 and 72° C., advantageously between 55 and 65° C.

The processes which are the subject of the present invention have very advantageous properties. In particular, they exhibit excellent reaction yields, generally greater than 95%. They benefit from total regioselectivity, i.e. a single regioisomer is formed during the reaction.

In order to prepare the pyrazoles of formula I, starting reagents comprising functional groups can be reacted without modifying them.

The reaction is applicable whatever the structure of the reagents defined above that are used.

The reaction is carried out under mild reaction conditions, compatible in particular with fragile molecules or biomolecules such as proteins, enzymes, DNA molecules, etc.

These properties are illustrated hereinafter in the experimental section. They justify the use of the processes described above, in the preparation of original pyrazole compounds, unobtainable up to now.

Consequently, a subject of the present application is also compounds of the pyrazole of formula I described above, in which R' and R" have the meaning and the preferred values already indicated and R represents a polypeptide, for instance angiotensin II, substance P, neurokine A, calcitoninin, oxytocin; a protein, for instance an antibody, an enzyme, hemoglobin, transferrin, streptavidin; a nucleic acid, for instance a molecule constituted of DNA or of RNA; a polysaccharide, for instance chitosan, cellulose, alginates, dextran; a polymer, for instance polyethylene glycol (PEG), polystyrene, polypropylene, polyethylene, polyacrylamide; a nanoparticle, for instance quantum dots, carbon nanotubes, metal nanoparticles (Au, $Fe_3O_4$, $Cr_2O_3$, $Al_2O_3$, $BaFe_{12}O_{19}$); a dendrimer, for instance PAMAM dendrimers, cyclotriphosphazene-PMMH.

In this case, R" preferably represents a radical which has a fluorophore function, for instance Cy3 and Cy5 cyanines, Alexa Fluor derivatives, coumarin derivatives, fluorescein derivatives and rhodamine derivatives, such as tetramethylrhodamine (TAMRA), a radiotracer, for instance DOTA-Gd, DOTA-Ga and DOTA-$^{64}$Cu complexes or a molecule comprising an $^{18}$F or $^{125}$I atom, an active ingredient of a human therapeutic (medicament), for instance taxol, taxotere, navelbine, vinblastine, a molecule capable of interacting with a protein or DNA, for instance biotin, tetraacetylfucose, RGD peptides, anthracyclines.

A subject of the present application is also compounds of the pyrazole of formula I described above, in which R and R' have the meaning and the preferred values already indicated and R" represents a polypeptide, for instance angiotensin II, substance P, neurokine A, calcitoninin, oxytocin; a protein, for instance an antibody, an enzyme, hemoglobin, transferrin, streptavidin; a nucleic acid, for instance a molecule constituted of DNA or of RNA; a polysaccharide, for instance chitosan, cellulose, alginates, dextran; a polymer, for instance polyethylene glycol (PEG), polystyrene, polypropylene, polyethylene, polyacrylamide; a nanoparticle, for instance quantum dots, carbon nanotubes, metal nanoparticles (Au, $Fe_3O_4$, $Cr_2O_3$, $Al_2O_3$, $BaFe_{12}O_{19}$); a dendrimer, for instance PAMAM dendrimers, cyclotriphosphazene-PMMH.

In this case, R preferably represents a radical which has a fluorophore function, for instance Cy3 and Cy5 cyanines, Alexa Fluor derivatives, coumarin derivatives, fluorescein derivatives and rhodamine derivatives, such as tetramethylrhodamine (TAMRA), a radiotracer, for instance DOTA-Gd, DOTA-Ga and DOTA-$^{64}$Cu complexes or a molecule comprising an $^{18}$F or $^{125}$I atom, an active ingredient of a human therapeutic (medicament), for instance taxol, taxotere, navelbine or vinblastine; a molecule capable of interacting with a protein or DNA, for instance biotin, tetraacetylfucose, RGD peptides, anthracyclines.

Whether with regard to the abovementioned preparation process or with regard to the novel compounds of the pyrazole of formula I above, the present invention does not cover the 1-(4-chlorophenyl)-4-pyridyl-2-pyrazole of Chunrul Wu.

The novel compounds of the pyrazole of formula I described above which are the subject of the present invention have very advantageous properties. In particular, they exhibit notable properties such as: 1) a high detection sensitivity in the case of the pyrazoles which have a group R or R"=fluorophore or radiotracer, ii) the capacity to effectively bind a biomolecule of interest in the case of the pyrazoles which have a group R or R"=active ingredient or a molecule capable of interacting with a protein or DNA.

These properties are illustrated hereinafter in the experimental section. They justify the use of the novel pyrazole compounds described above, in numerous applications, such as protein detection.

Consequently, a subject of the present application is also the use of the novel pyrazole compounds described above, as: i) biological tracers for medical imaging or diagnosis (triazoles comprising an $^{18}$F atom and an antibody for example), functional polymers for the capture and detection of biomolecules of interest, iii) molecules which allow the detection and analysis of DNA, of RNA and of proteins following the incorporation of fluorescent groups via the process of the invention, iv) nano-objects with therapeutic activity (in the case of dendrimers or of nanoparticles which have been polyfunctionalized, via the process of the invention, with an active ingredient), v) radiopharmaceutical compounds (triazoles comprising an antibody specific for tumor cells and a radioelement for example).

The preferential conditions for using the pyrazole compounds described above also apply to the other subjects of the invention targeted above, in particular to the applications thereof and also to the process for the production thereof.

The examples which follow illustrate the present application.

EXAMPLES 1 TO 6

Compounds of the pyrazole of formula I in which R represents a phenyl radical, R' represents a hydrogen atom and R" represents a benzyl radical were prepared in accordance with the reaction below,

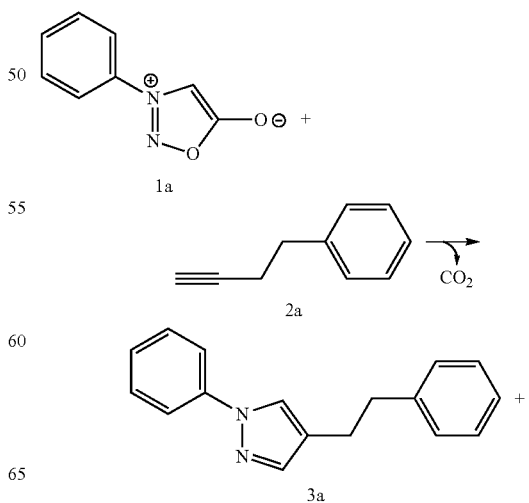

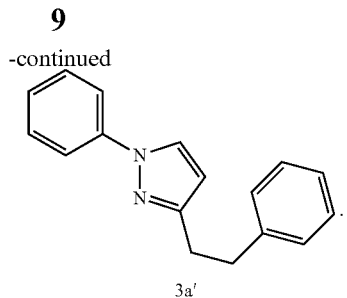

3a' according to the procedures of the invention set out below:

Procedure A

200 μl of a freshly prepared aqueous solution of copper sulfate pentahydrate (5 mg, 0.02 mmol) (0.2 eq.) in bathophenanthrolinedisulfonic acid disodium salt trihydrate (11.8 mg, 0.02 mmol) and triethanolamine (15 mg, 0.1 mmol) were added to a solution of sydnone (0.1 mmol), of alkyne (0.1 mmol), of sodium ascorbate (39.6 mg, 0.2 mmol) and of triethanolamine (15 mg, 0.1 mmol) in 1.8 ml of water. The resulting mixture was brought to 60° C. for 16 h with stirring, and then cooled with 2 ml of a 0.05 M solution of HEDTA and extracted with 3×5 ml of methylene chloride. The combined organic phases were dried over anhydrous sodium sulfate and concentrated so as to obtain the expected product, which was subjected to a further purification by flash chromatography.

Procedure B

A solution of sydnone (0.5 mmol), of alkyne (0.5 mmol), of triethylamine (0.5 mmol) and of 1,10-phenanthroline (0.1 mmol) in 10 ml of anhydrous dimethylformamide were poured into a flask containing copper iodide (0.1 mmol) under argon. The resulting mixture was brought to 60° C. under argon for 16 h, with stirring, and then concentrated. The residue was dissolved in 10 ml of methylene chloride and washed with 10 ml of a 0.05 M solution of HEDTA. The organic phase was dried over anhydrous sodium sulfate and concentrated to give the expected product, which was subjected to a further purification by flash chromatography.

Procedure C

Copper sulfate pentahydrate (5 mg, 0.02 mmol) (0.2 eq.) was added to a solution of sydnone (0.1 mmol), of alkyne (0.1 mmol), of sodium ascorbate (39.6 mg, 0.2 mmol), of triethylamine (0.1 mmol) and of 1,10-phenanthroline (0.02 mmol) in 2 ml of a tert-butanol/water mixture (1:1). The resulting mixture was stirred for 16 h at 60° C. and then cooled with 2 ml of a 0.05 M solution of HEDTA and extracted with 3×5 ml of methylene chloride. The combined organic phases were dried over anhydrous sodium sulfate and concentrated so as to obtain the expected product, which was subjected to a further purification by flash chromatography.

Procedure C'

200 μl of a freshly prepared aqueous solution of copper sulfate pentahydrate (5 mg, 0.02 mmol) (0.2 eq.) in bathophenanthrolinedisulfonic acid disodium salt trihydrate (11.8 mg, 0.02 mmol) and triethanolamine (15 mg, 0.1 mmol) were added to a solution of sydnone (0.1 mmol), of alkyne (0.1 mmol), and of sodium ascorbate (39.6 mg, 0.2 mmol) in 1.8 ml of a tert-butanol/water mixture (55:45). The resulting mixture was stirred for 16 h at 60° C. and then cooled with 2 ml of a 0.05 M solution of HEDTA and extracted with 3×5 ml of methylene chloride. The combined organic phases were dried over anhydrous sodium sulfate and concentrated so as to obtain the expected product, which was subjected to a further purification by flash chromatography.

Procedure D

The process was carried out as in procedure C, but by performing the reaction at ambient temperature.

Procedure E

The process was carried out as in procedure B, but without triethylamine.

Procedure F

The process was carried out as in procedure C, but without copper ligand (without 1,10-phenanthroline) and at 100° C. in place of 60° C.

Procedure G

The process was carried out as in procedure C, but using the ligand 3,10-diphenyldiimidazo[1,2-a:2',1'-c]quinoxaline (VIIIa) in place of 1,10-phenanthroline.

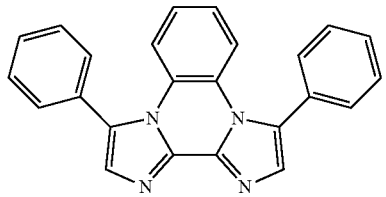

3,10-diphenyldiimidazo[1,2-a:2',1'-c]quinoxaline

The results obtained are reported in table 1 below.

TABLE 1

|  | % yield | 3a/3a' ratio |
| --- | --- | --- |
| Procedure A | 99 | 100/0 |
| Procedure B | 92 | 100/0 |
| Procedure C | 99 | 100/0 |
| Procedure C' | 99 | 100/0 |
| Procedure D | 67 | 100/0 |
| Procedure E | 62 | 100/0 |
| Procedure F | 16 | 100/0 |
| Procedure G | 40 | 100/0 |

Thus, an excellent yield is obtained, in particular using the protocols A, B, C and C', and in addition the regioselectivity of the reaction is complete in favor of the compound 3a, this being in very varied aqueous, organic or mixed media.

COMPARATIVE EXAMPLE 1

By way of comparison, the same reagents were also used to react them by the thermal route according to the prior art, under the following conditions: Solvent=DMF–Reflux (153° C.)–reaction time=16 h.

A yield of only 15% and a mixture of isomers 3a and 3a' in a 3a/3a' ratio=25/75 were obtained.

EXAMPLES 7 AND 8

4-phenethyl-1-phenyl-1H-pyrazole

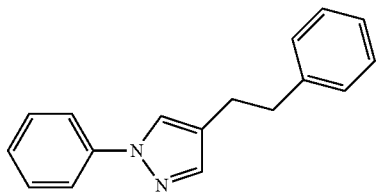 [SMILES: c1ccc(CCc2cnn(-c3ccccc3)c2)cc1]

The product of the title of example 7 was prepared from 3-phenylsydnone and 4-phenyl-1-butyne using procedure C, with purification by flash chromatography (ethyl acetate (EtOAc)/cyclohexane=20/80). The product was obtained in the form of a yellow oil with a yield of 96%.

By carrying out the process under the conditions of procedure B, the product was obtained with a yield of 90%.

$^1$H NMR (400 MHz, CDCl$_3$, δ ppm): 7.67 (s, 1 H), 7.65 (s, 2 H), 7.56 (s, 1 H), 7.46 (t, J=8.0 Hz, 2 H), 7.20-7.37 (m, 6 H), 2.93-3.00 (m, 2 H), 2.86-2.93 (m, 2 H).

$^{13}$C NMR (100 MHz, CDCl$_3$, δ ppm): 141.6, 141.0, 140.3, 129.5, 128.6, 128.5, 126.2, 125.0, 123.1, 118.9, 37.2, 26.3.

EXAMPLE 9

(1-phenyl-1H-pyrazol-4-yl)methyl benzoate

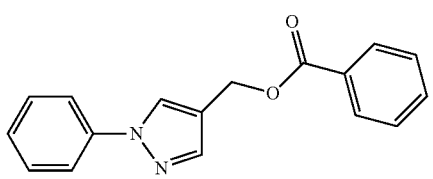 [SMILES: O=C(OCc1cnn(-c2ccccc2)c1)c1ccccc1]

The product of the title of example 9 was prepared from 3-phenylsydnone and prop-2-yn-1-yl benzoate using procedure C, with purification by flash chromatography (EtOAc/cyclohexane=20/80). The product was obtained in the form of a yellow oil with a yield of 93%.

$^1$H NMR (400 MHz, CDCl$_3$, δ ppm): 8.05 (m, 3 H), 7.82 (s, 1 H), 7.68 (d, J=7.7 Hz, 2 H), 7.56 (t, J=7.5 Hz, 1 H), 7.49-7.38 (m, 4 H), 7.30 (t, J=7.5 Hz, 1 H), 5.34 (s, 2 H).

$^{13}$C NMR (100 MHz, CDCl$_3$, δ ppm): 166.7, 141.7, 140.1, 133.2, 130.2, 129.8, 129.6, 128.5, 127.7, 126.9, 119.4, 118.6, 57.8.

EXAMPLE 10

2-(1-phenyl-1H-pyrazol-4-yl)propan-2-ol

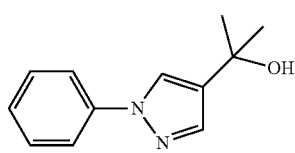

The product of the title of example 10 was prepared from 3-phenylsydnone and 2-methyl-3-butyn-2-ol using procedure C, with purification by flash chromatography (EtOAc/cyclohexane=10/90). The product was obtained in the form of a white solid with a yield of 83%.

$^1$H NMR (400 MHz, Methanol-d$_4$, δ ppm): 8.12 (s, 1 H), 7.75-7.65 (m, 3 H), 7.47 (t, J=8.1 Hz, 2 H), 7.31 (t, J=7.3 Hz, 1 H), 1.59 (s, 6 H).

$^{13}$C NMR (100 MHz, Methanol-d$_4$, δ ppm): 141.6, 139.7, 135.0, 130.7, 127.8, 125.7, 120.4, 68.7, 31.9.

EXAMPLE 11

1,4-diphenyl-1H-pyrazole

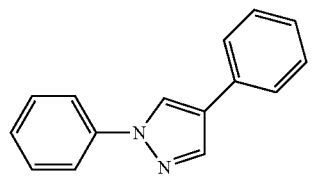 [SMILES: c1ccc(-c2cnn(-c3ccccc3)c2)cc1]

The product of the title of example 11 was prepared from 3-phenylsydnone and phenylacetylene using procedure C, with purification by flash chromatography (EtOAc/cyclohexane=20/80). The product was obtained in the form of a white solid with a yield of 80%.

$^1$H NMR (400 MHz, CDCl$_3$, δ ppm): 8.19 (s, 1 H), 8.04 (s, 1 H), 7.77 (d, J=8.1 Hz, 2 H), 7.59 (d, J=7.7 Hz, 2 H), 7.51 (t, J=7.8 Hz, 2 H), 7.44 (t, J=7.7 Hz, 2 H), 7.37-7.27 (m, 2 H).

$^{13}$C NMR (100 MHz, CDCl$_3$, δ ppm): 140.2, 138.9, 132.2, 129.6, 129.1, 127.0, 126.7, 125.8, 125.0, 123.5, 119.2.

EXAMPLE 12

4-heptyl-1-phenyl-1H-pyrazole

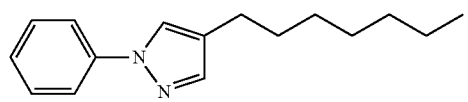 [SMILES: CCCCCCCc1cnn(-c2ccccc2)c1]

The product of the title of example 12 was prepared from 3-phenylsydnone and 1-nonyne using procedure C', with purification by flash chromatography (EtOAc/cyclohexane=20/80). The product was obtained in the form of a yellow oil with a yield of 61%.

$^1$H NMR (400 MHz, CDCl$_3$, δ ppm): 7.70 (s, 1 H), 7.66 (d, J=7.7 Hz, 2 H), 7.55 (s, 1 H), 7.43 (t, J=7.9 Hz, 2 H), 7.25 (t, J=7.3 Hz, 1 H), 2.52 (t, J=7.7 Hz, 2 H), 1.61 (quin, J=7.4 Hz, 2 H), 1.38-1.28 (m, 8 H), 0.89 (t, J=6.8 Hz, 3 H).

$^{13}$C NMR (100 MHz, CDCl$_3$, δ ppm): 141.1, 140.4, 129.5, 126.1, 124.8, 124.2, 118.9, 32.0, 30.9, 29.4, 29.3, 24.3, 22.8, 14.2.

EXAMPLE 13

4-(4-phenethyl-1H-pyrazol-1-yl)benzoic acid

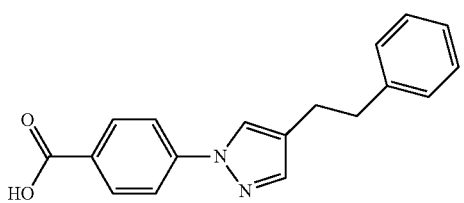 [SMILES: O=C(O)c1ccc(-n2cc(CCc3ccccc3)cn2)cc1]

The product of the title of example 13 was prepared from 3-(4-carboxyphenyl)sydnone and 4-phenyl-1-butyne using procedure C'. The product was obtained in the form of a white solid with a yield of 99%.

$^1$H NMR (400 MHz, DMSO-$d_6$, δ ppm): 12.98 (br. s., 1 H), 8.40 (s, 1 H), 8.04 (d, J=8.6 Hz, 2 H), 7.90 (d, J=8.6 Hz, 2 H), 7.63 (s, 1 H), 7.32-7.21 (m, 4 H), 7.17 (t, J=6.8 Hz, 1 H), 2.90 (t, J=7.7 Hz, 2 H), 2.79 (t, J=7.7 Hz, 2 H).

$^{13}$C NMR (100 MHz, DMSO-$d_6$, δ ppm): 166.7, 142.8, 141.8, 141.4, 130.9, 128.3, 128.3, 127.7, 126.0, 125.9, 123.6, 117.4, 36.0, 25.6.

EXAMPLES 14, 15, 16

4-(4-(2-hydroxypropan-2-yl)-1H-pyrazol-1-yl)benzoic acid

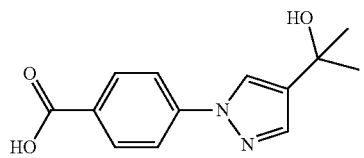 [SMILES: CC(C)(O)c1cnn(-c2ccc(C(=O)O)cc2)c1]

The product of the title of example 14 was prepared from 3-(4-carboxyphenyl)sydnone and 2-methyl-3-butyn-2-ol using procedure A, with the process being carried out at 37° C. The product was obtained in the form of a white solid with a yield of 93%.

By carrying out the process under the conditions of procedure A but using human blood plasma as solvent, the product was obtained with a yield of 88%.

By carrying out the process under the conditions of procedure C, the product was obtained with a yield of 91%.

$^1$H NMR (400 MHz, Methanol-$d_4$, δ ppm): 8.27 (s, 1 H), 8.14 (d, J=8.8 Hz, 2 H), 7.87 (d, J=8.8 Hz, 2 H), 7.77 (s, 1 H), 1.61 (s, 6 H)

$^{13}$C NMR (100 MHz, Methanol-$d_4$, δ ppm): 169.2, 144.8, 140.7, 135.7, 132.5, 125.6, 119.4, 68.7, 31.9.

EXAMPLE 17

(2R,3R,4S,5R,6R)-2-(acetoxymethyl)-6-((1-phenyl-1H-pyrazol-4-yl)methoxy)tetrahydro-2H-pyran-3,4,5-triyl triacetate

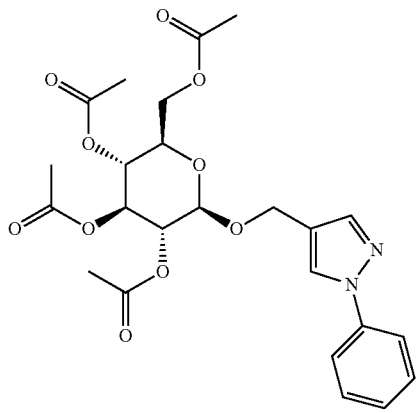 [SMILES: CC(=O)OC[C@H]1O[C@@H](OCc2cnn(-c3ccccc3)c2)[C@H](OC(C)=O)[C@@H](OC(C)=O)[C@@H]1OC(C)=O]

The product of the title of example 17 was prepared from 3-(phenyl)sydnone and 2-propynyl-tetra-O-acetyl-β-D-glucopyranoside using procedure C. The product was obtained in the form of a white solid with a yield of 96%.

$^1$H NMR (400 MHz, CDCl$_3$, δ ppm): 7.89 (s, 1 H), 7.68-7.62 (m, 3 H), 7.44 (t, J=7.9 Hz, 2 H), 7.28 (t, J=7.2 Hz, 1 H), 5.19 (t, J=9.5 Hz, 1 H), 5.10 (t, J=9.5 Hz, 1 H), 5.03 (t, J=9.1 Hz, 1 H), 4.83 (d, J=12.4 Hz, 1 H), 4.66-4.59 (m, 2 H), 4.27 (dd, J=4.8, 12.2 Hz, 1 H), 4.18 (dd, J=2.3, 12.2 Hz, 1 H), 3.76-3.66 (m, 1 H), 2.09 (s, 3 H), 2.01 (s, 3 H), 1.99 (s, 3 H), 1.98 (s, 3 H).

$^{13}$C NMR (100 MHz, CDCl$_3$, δ ppm): 170.8, 170.3, 169.5, 169.4, 140.9, 140.0, 129.5, 126.8, 126.6, 119.2, 119.0, 99.2, 72.9, 71.9, 71.3, 69.2, 68.5, 62.1, 62.0, 20.8, 20.7, 20.6.

EXAMPLE 18

4-(4-methoxyphenyl)-1-phenyl-1H-pyrazole

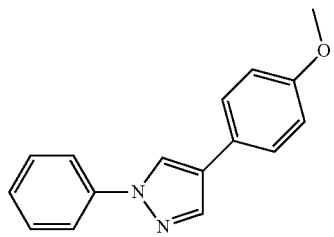 [SMILES: COc1ccc(-c2cnn(-c3ccccc3)c2)cc1]

The product of the title of example 18 was prepared from 3-(phenyl)sydnone and 1-ethynyl-4-methoxybenzene using procedure C', with purification by flash chromatography (EtOAc/cyclohexane=20/80). The product was obtained in the form of a white solid with a yield of 64%.

$^1$H NMR (400 MHz, CDCl$_3$, δ ppm): 8.09 (s, 1 H), 7.94 (s, 1 H), 7.73 (d, J=8.2 Hz, 2 H), 7.48 (t, J=8.2 Hz, 4 H), 7.30 (t, J=7.3 Hz, 1 H), 6.95 (d, J=8.6 Hz, 2 H), 3.85 (s, 3 H).

$^{13}$C NMR (100 MHz, CDCl$_3$, δ ppm): 158.8, 140.2, 138.7, 129.6, 127.1, 126.7, 124.8, 124.8, 123.0, 119.2, 114.6, 55.5.

EXAMPLE 19

2-(1-phenyl-1H-pyrazol-4-yl)pyridine

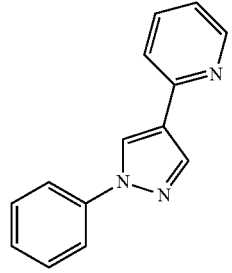 [SMILES: c1ccc(-n2cc(-c3ccccn3)cn2)cc1]

The product of the title of example 19 was prepared from 3-(phenyl)sydnone and 2-ethynylpyridine using procedure C'. The product was obtained in the form of a white solid with a yield of 95%.

$^1$H NMR (400 MHz, CDCl$_3$, δ ppm): 8.62 (d, J=4.8 Hz, 1 H), 8.55 (s, 1 H), 8.20 (s, 1 H), 7.78 (d, J=7.9 Hz, 2 H), 7.72 (dt, J=1.6, 7.7 Hz, 1 H), 7.57 (d, J=8.1 Hz, 1 H), 7.50 (t, J=8.0 Hz, 2 H), 7.33 (t, J=7.3 Hz, 1 H), 7.20-7.12 (m, 1 H).

$^{13}$C NMR (100 MHz, CDCl$_3$, δ ppm): 151.5, 149.7, 140.0, 139.3, 136.9, 129.6, 126.9, 125.4, 125.2, 121.6, 119.9, 119.3.

EXAMPLE 20

1-phenyl-4-(thiophen-3-yl)-1H-pyrazole

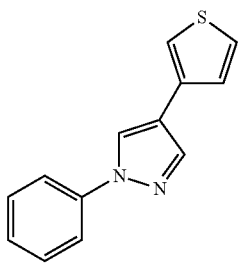 [SMILES: c1ccc(-n2cc(-c3ccsc3)cn2)cc1]

The product of the title of example 20 was prepared from 3-(phenyl)sydnone and 2-ethynylthiophene using procedure C'. The product was obtained in the form of a white solid with a yield of 99%.

$^1$H NMR (400 MHz, CDCl$_3$, δ ppm): 8.11 (s, 1 H), 7.95 (s, 1 H), 7.75 (d, J=8.0 Hz, 2 H), 7.49 (t, J=8.0 Hz, 2 H), 7.42-7.38 (m, 1 H), 7.38-7.27 (m, 3 H).

$^{13}$C NMR (100 MHz, CDCl$_3$, δ ppm): 140.1, 139.2, 132.9, 129.6, 126.6, 126.4, 126.2, 123.4, 120.4, 119.1, 115.1.

EXAMPLE 21

4-(4-((5-(dimethylamino)naphthalene-1-sulfonamido)-methyl)-1H-pyrazol-1-yl)benzoic acid

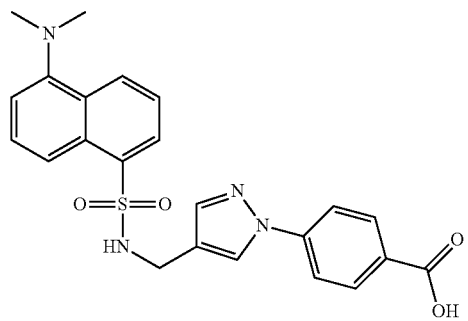 [SMILES: CN(C)c1cccc2c(S(=O)(=O)NCc3cnn(-c4ccc(C(=O)O)cc4)c3)cccc12]

The product of the title of example 21 was prepared from 3-(4-carboxyphenyl)sydnone and 5-(dimethylamino)-N-(prop-2-yn-1-yl)naphthalene-1-sulfonamide using procedure C', with the process being carried out at 37° C., and with purification by flash chromatography (EtOAc/cyclohexane/AcOH=49/49/2). The product was obtained in the form of a yellow solid with a yield of 59%.

$^1$H NMR (400 MHz, Methanol-d$_4$, δ ppm): 8.40 (d, J=8.4 Hz, 1 H), 8.28 (d, J=8.6 Hz, 1 H), 8.20 (d, J=7.4 Hz, 1 H), 8.03 (d, J=8.8 Hz, 2 H), 7.59-7.42 (m, 5 H), 7.20 (s, 1 H), 7.17 (d, J=7.5 Hz, 1 H), 4.10 (s, 2 H), 2.73 (s, 6 H).

$^{13}$C NMR (100 MHz, Methanol-d$_4$, δ ppm): 169.2, 153.3, 144.1, 142.3, 137.5, 132.3, 131.4, 131.1, 131.1, 130.7, 129.9, 129.2, 127.7, 124.3, 121.9, 120.5, 119.2, 116.4, 45.8, 38.0.

EXAMPLE 22

2-(6-(diethylamino)-3-(diethyliminio)-3H-xanthen-9-yl)-5-(N-((1-phenyl-1H-pyrazol-4-yl)methyl)sulfamoyl)benzenesulfonate

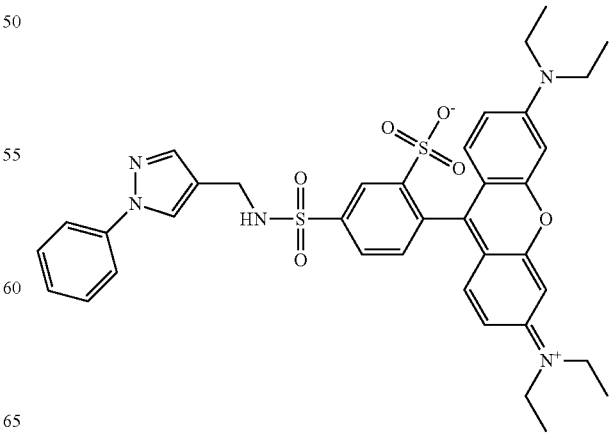

The product of the title of example 22 was prepared from 3-(phenyl)sydnone and 2-(6-(diethylamino)-3-(diethylimino)-3H-xanthen-9-yl)-5-(N-(prop-2-yn-1-yl)sulfamoyl)benzenesulfonate using procedure C' and isolation by filtration from the reaction medium. The product was obtained in the form of a violet solid with a yield of 92%.

$^1$H NMR (400 MHz, DMSO-d$_6$, δ ppm): 8.47 (d, J=1.6 Hz, 1 H), 8.38 (br. s., 1 H), 8.32 (s, 1 H), 7.91 (dd, J=1.6, 8.0 Hz, 1 H), 7.76 (d, J=7.9 Hz, 2 H), 7.51 (s, 1 H), 7.45 (t, J=7.9 Hz, 2 H), 7.39 (d, J=7.9 Hz, 1 H), 7.28 (t, J=7.3 Hz, 1 H), 6.98-6.86 (m, 6 H), 4.12 (d, J=2.8 Hz, 2 H), 3.69-3.56 (m, 8 H), 1.20 (t, J=7.0 Hz, 12 H).

MS (ESI) m/z: 714.3 [M+H]$^+$.

sulfate and concentrated so as to obtain 127.3 mg of the expected product in the form of a white solid, 0.26 mmol, yield 85%, which was subjected to a further purification by flash chromatography (CH$_2$Cl$_2$/EtOAc=80/20 to 0/100).

$^1$H NMR (400 MHz, CDCl$_3$, δ ppm): 7.91 (s, 3 H), 7.73 (s, 3 H), 7.71 (d, J=8.0 Hz, 6 H), 7.47 (t, J=7.9 Hz, 6 H), 7.30 (t, J=8.2 Hz, 3 H), 3.67 (s, 6 H).

$^{13}$C NMR (100 MHz, CDCl$_3$, δ ppm): 141.7, 140.2, 129.6, 126.5, 126.4, 120.3, 119.0, 47.1.

EXAMPLE 24 labeling of a peptide with a fluorophore: 2-(2-(2-(4-(4-((5-(dimethylamino)naphthalene-1-sulfonamido)methyl)-1H-pyrazol-1-yl)-benzamido)acetamido)-3-(1H-indol-3-yl)propanamido)acetic acid

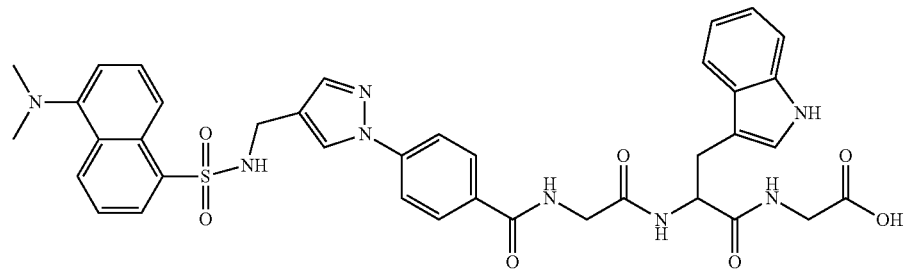

EXAMPLE 23 tris((1-phenyl-1H-pyrazol-4-yl)methyl)amine

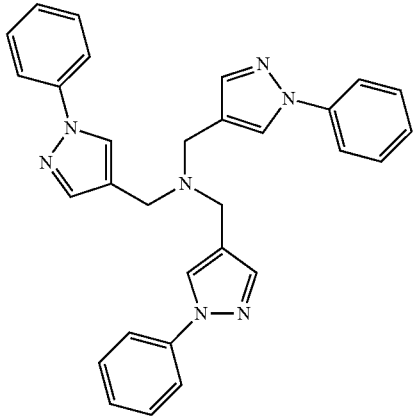 [SMILES: c1ccc(-n2cc(CN(Cc3cnn(-c4ccccc4)c3)Cc3cnn(-c4ccccc4)c3)cn2)cc1]

Copper sulfate pentahydrate (0.15 mmol) was added to a solution of 3-phenylsydnone (0.9 mmol), tripropargylamine (0.1 mmol), sodium ascorbate (1.5 mmol), triethylamine (0.9 mmol) and 1,10-phenanthroline (0.15 mmol) in 18 ml of a tert-butanol/water mixture (1:1).

The resulting mixture was stirred in a closed flask at 60° C. for 16 h. The second portion of sodium ascorbate (1.5 mmol), of 1,10-phenanthroline (0.15 mmol) and of the copper sulfate pentahydrate (0.15 mmol) was then added to the mixture and the new mixture was stirred at 60° C. for a further 24 h.

After cooling to ambient temperature, the mixture was diluted with 20 ml of a 0.05 M solution of HEDTA and was extracted with 3×30 ml of methylene chloride. The combined organic phases were dried over anhydrous sodium 200 µl of a freshly prepared aqueous solution of copper sulfate pentahydrate (0.9 mg, 3.6 µmol), bathophenanthrolinedisulfonic acid disodium salt trihydrate (2.1 mg, 3.6 µmol) and triethanolamine (1.8 mg, 12 µmol) were added to a solution of 3-(4-((2-(((1-((carboxymethyl)amino)-3-(1H-indol-3-yl)-1-oxopropan-2-yl)amino)-2-oxoethyl)carbamoyl)phenyl)-1,2,3-oxadiazol-3-ium-5-olate (6 mg, 12 µmol), N-dansyl-N-propargylamine (4.5 mg, 16 µmol), sodium ascorbate (7 mg, 36 µmol) and triethanolamine (1.8 mg, 12 µmol) in 1 ml of water. The resulting mixture was stirred at 37° C. for 16 h. A liquid chromatography/mass spectrometry analysis of the resulting mixture showed complete conversion of the starting product. The mixture was concentrated and purified by high performance liquid chromatography on a C18 XBridge 19×150 mm, 5 µm column so as to give the expected product labeled with dansyl.

$^1$H NMR (400 MHz, Methanol-d$_4$, δ ppm): 8.43 (d, J=8.4 Hz, 1 H), 8.30 (d, J=8.6 Hz, 1 H), 8.22 (d, J=6.6 Hz, 1 H), 7.86 (d, J=8.8 Hz, 2 H), 7.63-7.55 (m, 3 H), 7.54-7.46 (m, 3 H), 7.31 (d, J=8.1 Hz, 1 H), 7.22 (s, 1 H), 7.20 (d, J=7.5 Hz, 1 H), 7.16 (s, 1 H), 7.07 (t, J=7.1 Hz, 1 H), 7.00 (t, J=7.5 Hz, 1 H), 4.80 (dd, J=5.4, 7.8 Hz, 1 H), 4.12 (s, 2 H), 4.06 (d, J=16.5 Hz, 1 H), 4.01-3.83 (m, 3 H), 3.44-3.38 (m, 1 H), 3.25-3.12 (m, 1 H), 2.76 (s, 6 H).

MS (ESI) m/z: 751.4 [M+H]$^+$.

EXAMPLE 25

Labeling of a Protein with a Fluorophore

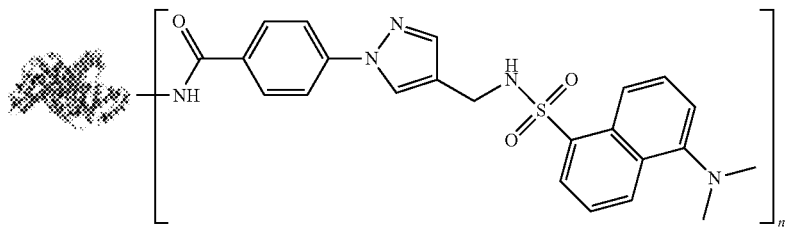

The process was carried out as above, but using, as starting sydnone, the sydnone coupled to bovine serum albumin prepared hereinafter. The process was carried out at ambient temperature for 16 h under the following conditions:

Sydnone coupled to bovine serum albumin: 1 mg/ml-0.18 µmol, 1 eq.

N-dansyl-N-propargylamine: 1.8 µmol, 10 eq.

CuSO$_4$: 1.8 µmol, 10 eq.

Bathophenanthroline: 1.8 µmol, 10 eq.

Sodium ascorbate: 18 µmol, 100 eq.

After revealing the proteins with Coomassie blue and measuring the fluorescence of the dansyl $\lambda_{ex}$=320 nm, $\lambda_{em}$=320 nm, it was found that an average number of dansyl residues of 1.6 were grafted onto the bovine serum albumin.

Thus, the process of the invention can be carried out on starting sydnones carrying biological molecules.

EXAMPLE 26

(R)-(1-phenyl-1H-pyrazol-4-yl)methyl 2-(4-((5-chloro-3-fluoropyridin-2-yl)oxy)phenoxy)propanoate

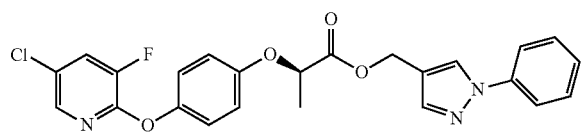 [SMILES: C[C@@H](Oc1ccc(Oc2ncc(Cl)cc2F)cc1)C(=O)OCc1cnn(-c2ccccc2)c1]

The product of the title of example 26 was prepared from 3-(phenyl)sydnone and clodinafop-propargyl using procedure C' with purification by flash chromatography (EtOAc/cyclohexane=30/70). The product was obtained in the form of a white solid with a yield of 62%.

$^1$H NMR (400 MHz, Methanol-d$_4$, δ ppm): 8.15 (s, 1 H), 7.79 (d, J=2.2 Hz, 1 H), 7.75 (dd, J=2.2, 9.5 Hz, 1 H), 7.70 (s, 1 H), 7.66 (d, J=7.9 Hz, 2 H), 7.44 (t, J=7.9 Hz, 2 H), 7.30 (t, J=7.3 Hz, 1 H), 6.99 (d, J=9.0 Hz, 2 H), 6.86 (d, J=9.0 Hz, 2 H), 5.19 (s, 2 H), 4.85 (q, J=6.8 Hz, 1 H), 1.58 (d, J=6.8 Hz, 3 H).

$^{13}$C NMR (100 MHz, CDCl$_3$, δ ppm): 173.8, 156.4, 152.7, 148.6, 148.5, 142.7, 141.3, 141.2, 130.7, 129.6, 128.1, 126.5, 126.3, 123.4, 120.5, 119.8, 117.2, 74.3, 59.0, 18.9.

MS (ESI) m/z: 468.0 [M($^{35}$Cl)+H]$^+$, 469.8 [M($^{37}$Cl)+H]$^+$.

EXAMPLE 27

1-((2R,4S,5R)-4-hydroxy-5-(hydroxymethyl)tetrahydrofuran-2-yl)-5-(1-phenyl-1H-pyrazol-4-yl)pyrimidine-2,4(1H,3H)-dione

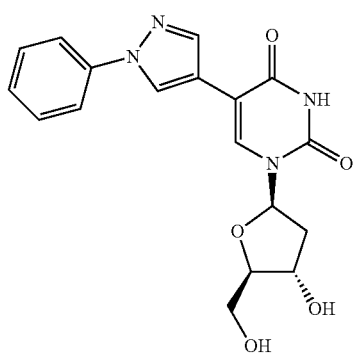 [SMILES: O=c1[nH]c(=O)n([C@H]2C[C@H](O)[C@@H](CO)O2)cc1-c1cnn(-c2ccccc2)c1]

The product of the title of example 27 was prepared from 3-(phenyl)sydnone and 5-ethynyl-2'-deoxyuridine using procedure C' and isolation by filtration from the reaction medium. The product was obtained in the form of a white solid with a yield of 84%.

$^1$H NMR (400 MHz, DMSO-d6, δ ppm): 8.68 (s, 1 H), 8.48 (s, 1 H), 8.05 (s, 1 H), 7.81 (d, J=7.9 Hz, 2 H), 7.50 (t, J=7.9 Hz, 2 H), 7.32 (t, J=7.9 Hz, 1 H), 6.23 (t, J=6.4 Hz, 1 H), 4.33 (br. s, 1 H), 3.84 (d, J=3.0 Hz, 1 H), 3.73 (dd, J=3.0, 11.9 Hz, 1 H), 3.66 (dd, J=3.0, 11.9 Hz, 1 H), 2.32-2.13 (m, 2 H).

$^{13}$C NMR (100 MHz, DMSO-d$_6$, δ ppm): 162.1, 150.0, 139.9, 138.9, 135.8, 130.0, 126.7, 124.9, 118.7, 116.6, 106.2, 87.8, 85.0, 70.2, 61.1, 31.0.

MS (ESI) m/z: 371.0 [M+H]$^+$, 741.3 [2M+H]$^+$.

EXAMPLE 28 ethyl 1-phenyl-1H-pyrazole-4-carboxylate

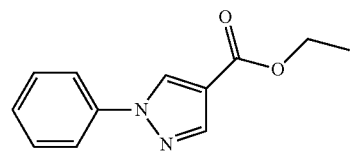 [SMILES: CCOC(=O)c1cnn(-c2ccccc2)c1]

The product of the title of example 28 was prepared from 3-phenylsydnone and ethyl propionate using protocol F. The product was obtained with a yield of 84% after purification by chromatography (EtOAc/cyclohexane=10/90).

$^1$H NMR (400 MHz, CDCl$_3$, δ ppm): 8.39 (s, 1H), 8.08 (s, 1H), 7.68 (d, J=8.0 Hz, 2H), 7.45 (t, J=8.0 Hz, 2H), 7.32 (t, J=7.3 Hz, 1H), 4.32 (q, J=7.1 Hz, 2H), 1.36 (t, J=7.1 Hz, 3H).

$^{13}$C NMR (100 MHz, CDCl$_3$, δ ppm): 162.9, 142.2, 139.4, 130.0, 129.6, 127.6, 119.6, 117.0, 60.5, 14.5.

IR (NaCl, cm$^{-1}$): 3124, 3063, 2984, 2901, 1709, 1597, 1560, 1505, 1463, 1413, 1390, 1258, 1150, 1027, 996, 951, 887, 825, 770, 757, 688, 654.

MS (ESI) m/z: 217.1[M+H]$^+$.

HRMS (ESI) m/z: calc. for C$_{12}$H$_{13}$N$_2$O$_2$: 217.0977; found: 217.0971.

EXAMPLE 29

5-bromo-4-phenethyl-1-phenyl-1H-pyrazole

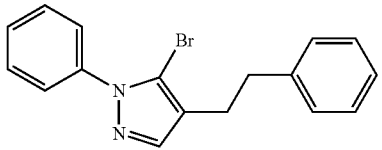 [SMILES: Brc1c(CCc2ccccc2)cnn1-c1ccccc1]

The product of the title of example 29 was prepared from 3-phenyl-4-bromosydnone and 4-phenyl-1-butyne using protocol G. The product was obtained in the form of a yellow solid with a yield of 74% after purification by chromatography (heptane/ethyl acetate: 95/5).

$^1$H NMR (Chloroform-d, 400 MHz): d=7.38-7.55 (m, 6 H), 7.28-7.34 (m, 2 H), 7.19-7.25 (m, 3 H), 2.89-2.95 (m, 2 H), 2.77-2.83 (m, 2 H) ppm;

$^{13}$C NMR (Chloroform-d, 101 MHz): d=141.4, 140.9, 139.4, 129.0, 128.6, 128.6, 128.3, 126.3, 125.6, 122.3, 112.6, 36.3, 26.7 ppm;

IR (NaCl, cm$^{-1}$): 3062, 3027, 2923, 2856, 1598, 1556, 1499, 1455, 1407, 1391, 1241, 1087, 1068, 961, 911, 851, 836, 760, 694;

LCMS (ESI) C$_{17}$H$_{15}$BrN$_2$ (M[$^{79}$Br]+H) 326.9, (M[$^{81}$Br]+H) 328.8.

EXAMPLE 30

5-bromo-1-(4-methoxyphenyl)-4-phenethyl-1H-pyrazole

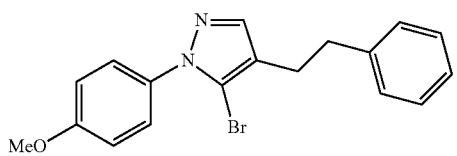 [SMILES: COc1ccc(-n2ncc(CCc3ccccc3)c2Br)cc1]

The product of the title of example 30 was prepared from 3-(p-methoxyphenyl)-4-bromosydnone and 4-phenyl-1-butyne using protocol G. The product was obtained in the form of a yellow solid with a yield of 70% after purification by chromatography (heptane/ethyl acetate: 95/5).

$^1$H NMR (Chloroform-d, 400 MHz): d=7.49 (s, 1 H), 7.39-7.44 (m, 2 H), 7.28-7.34 (m, 2 H), 7.19-7.25 (m, 3 H), 6.95-7.01 (m, 2 H), 3.86 (s, 3 H), 2.88-2.95 (m, 2 H), 2.75-2.82 (m, 2 H) ppm;

$^{13}$C NMR (Chloroform-d, 101 MHz): d=159.4, 141.3, 140.3, 132.4, 128.6 (2C), 128.4 (2C), 127.0 (2C), 126.1, 121.7, 114.0 (2C), 112.9, 55.6, 36.1, 26.7 ppm; LCMS (ESI) C$_{18}$H$_{17}$BrN$_2$O (M[$^{79}$Br]+H) 357.3, (M[$^{81}$Br]+H) 359.4.

The starting sydnones of formula II can be prepared as follows:

Stage A: Preparation of N-Nitrosylated Amino Acids

A solution of 6.90 g of NaNO$_2$ in 100 ml of water is added dropwise, over the course of 40 minutes, to a vigorously stirred suspension of N-aryl amino acid (0.1 mol) in 10% aqueous hydrochloric acid (100 ml). The resulting mixture was stirred at ambient temperature under nitrogen for 14 h. The expected product was recovered by filtration, washed with a small amount of methanol and dried so as to produce the expected N-nitrosylated compound.

4-((carboxymethyl)(nitroso)amino)benzoic acid was thus prepared in the form of a white solid with a yield of 72%.

$^1$H NMR (400 MHz, DMSO-d$_6$, δ ppm): 8.08 (d, J=8.6 Hz, 2 H), 7.76 (d, J=8.6 Hz, 2 H), 4.81 (s, 2 H).

$^{13}$C NMR (100 MHz, DMSO-d$_6$, δ ppm): 167.0, 166.6, 144.5, 130.7, 129.3, 119.0, 46.2.

2-(nitroso(phenyl)amino)acetic acid was also prepared in the form of a white solid with a yield of 89%.

$^1$H NMR (400 MHz, DMSO-d$_6$, δ ppm): 7.62 (d, J=7.9 Hz, 2 H), 7.54 (t, J=7.9 Hz, 2 H), 7.43 (t, J=7.3 Hz, 1 H), 4.76 (s, 2 H).

$^{13}$C NMR (100 MHz, DMSO-d$_6$, δ ppm): 167.2, 141.3, 129.5, 127.6, 119.9, 46.9.

Stage B: Preparation of Sydnones of Formula II

A mixture of 0.1 mol of N-nitrosylated amino acid and 100 ml of acetic anhydride was mixed for 3 h at 100°. The solution obtained was concentrated on a rotary evaporator. The residue was triturated with 100 ml of water. The precipitate was then recovered by filtration and recrystallized from methanol so as to obtain the expected pure product.

3-(4-carboxyphenyl)-1,2,3-oxadiazol-3-ium-5-olate was thus prepared in the form of a white solid with a yield of 52%.

$^1$H NMR (400 MHz, DMF-d$_7$, δ ppm): 8.32 (d, J=8.5 Hz, 2 H), 8.19 (d, J=8.5 Hz, 2 H), 7.88 (s, 1 H).

$^{13}$C NMR (100 MHz, DMF-d$_7$, δ ppm): 169.7, 167.1, 138.9, 135.7, 132.3, 123.1, 96.1.

3-phenyl-1,2,3-oxadiazol-3-ium-5-olate was also prepared in the form of a white solid with a yield of 55%.

$^1$H NMR (400 MHz, DMSO-d$_6$, δ ppm): 7.94 (dd, J=1.5, 8.1 Hz, 2 H), 7.78 (s, 1 H), 7.77-7.67 (m, 3 H).

$^{13}$C NMR (100 MHz, DMSO-d$_6$, δ ppm): 168.5, 132.4, 130.2, 126.6, 121.6, 94.9.

Preparation of a sydnone of formula II carrying a tripeptide: 3-(4-((2-((1-((carboxymethyl)amino)-3-(1H-indol-3-yl)-1-oxopropan-2-yl)amino)-2-oxoethyl)carbamoyl)phenyl)-1,2,3-oxadiazol-3-ium-5-olate

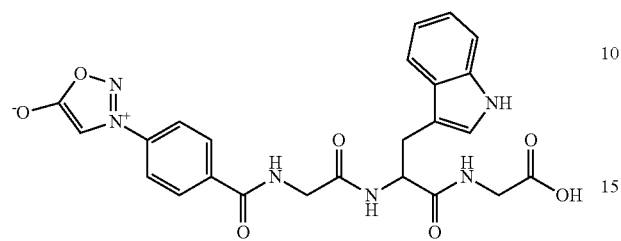

N,N'-dicyclohexylcarbodiimide (13 mg, 0.063 mmol) was added to a solution of 3-(4-carboxyphenyl)sydnone (13 mg, 0.063 mmol) and of N-hydroxysuccinimide (8.7 mg, 0.076 mmol) in anhydrous dimethylformamide (1 ml) at 0° C. The resulting solution was stirred at ambient temperature for 24 h and was then filtered. The tripeptide H-Gly-Trp-Gly-OH (20 mg, 0.063 mmol) was then added to the filtrate and the solution was stirred at ambient temperature for a further 16 h. The mixture was then concentrated and the residue was purified by semi-preparative high performance liquid chromatography on a Phenomenex Synergi Fusion-RP 21.2×150 mm, 5 μm column so as to produce 13 mg of the expected product in the form of a white solid with a yield of 41%.

$^1$H NMR (400 MHz, Methanol-$d_4$, δ ppm): 8.05 (d, J=8.8 Hz, 2 H), 7.98 (d, J=8.8 Hz, 2 H), 7.58 (d, J=8.8 Hz, 1 H), 7.48 (s, 1 H), 7.28 (d, J=8.1 Hz, 1 H), 7.14 (s, 1 H), 7.04 (t, J=7.3 Hz, 1 H), 6.97 (t, J=7.2 Hz, 1 H), 4.79 (dd, J=5.5, 7.7 Hz, 1 H), 4.07 (d, J=16.5 Hz, 1 H), 3.97 (d, J=16.5 Hz, 1 H), 3.94-3.82 (m, 2 H), 3.36 (dd, J=5.2, 14.7 Hz, 1 H), 3.17 (dd, J=8.1, 14.8 Hz, 1 H).

MS (ESI) m/z: 507.1 [M+H]$^+$.

Preparation of a Sydnone of Formula II Carrying a Protein: Bovine Serum Albumin (BSA)

The process was carried out as above, but using bovine serum albumin instead of the tripeptide, so as to obtain the expected product, in which the bovine serum albumin carries 12 sydnones.

The invention claimed is:

1. A process for preparing a pyrazole of formula I in which
R represents a hydrogen atom; a halogen atom; a thio or -thioalkyl group; a hydroxyl or alkoxy group; an amino or -aminoalkyl group; an alkyl radical containing from 1 to 8 carbon atoms which is unsubstituted or substituted one or more times with F, Cl, Br, I , CN, OH, NH2, NH—(C1-C8 alkyl), N—(C1-C8 alkyl)2, SH; an aryl radical containing 6 to 10 carbon atoms which is unsubstituted or substituted one or more times with an alkyl or alkoxy radical containing 1 to 8 carbon atoms; a heterocycle; an amino acid; a polypeptide; a protein; a nucleic acid; a DNA molecule; a polysaccharide; a polymer; a nanoparticle; a dendrimer;

R' represents a hydrogen atom; a halogen atom; a thio or -thioalkyl group; a hydroxyl or, alkoxy group; an amino or -aminoalkyl group; an alkyl radical containing from 1 to 8 carbon atoms which is unsubstituted or substituted one or more times with F, Cl, Br, I, CN, OH, NH2, NH—(C1-C8 alkyl), N—(C1-C8 alkyl) 2, SH; an aryl radical containing 6 to 10 carbon atoms which is unsubstituted or substituted one or more times with an alkyl or alkoxy radical containing 1 to 8 carbon atoms; a heterocycle;

R" represents a hydrogen atom; a halogen atom; a thio group; a hydroxyl group; an amino group; a hydrocarbon-based group or a hydrocarbon-based group containing from 1 to 100 heteroatoms;

wherein a sydnone of formula II in which R and R' have be meanings already indicated, is reacted with an alkyne of formula III

R"———    III in which R" has the meaning already indicated, in the presence of copper salt complexed with a nitrogenous ligand used as a catalyst metal, so as to obtain a pyrazole compound of formula I which is isolated and salified if desired.

2. A process as claimed in claim 1, wherein R represents an unsubstituted or substituted aryl or heteroaryl radical.

3. A process as claimed in claim 1, wherein R' represents a hydrogen atom.

4. A process as claimed in claim 1, wherein R" represents a hydrogen atom; a halogen atom; a thio or -thioalkyl group; a hydroxyl or alkoxy group; an amino or -aminoalkyl group; an alkyl radical containing from 1 to 8 carbon atoms which is unsubstituted or substituted one or more times with F, Cl, Br, I, CN, OH, —O-heterocycle which is substituted or unsubstituted, NH2, —NH—(C1-C8 alkyl), —N—(C1-C8 alkyl)2, —NH—R''' or —(C1-C3 alkyl)—NH—R''' where R''' represents a sulfonated group, SH; an aryl radical containing 6 to 10 carbon atoms which is unsubstituted or substituted one or more times with an alkyl or alkoxy radical containing 1 to 8 carbon atoms; a heterocycle; an amino acid; a. polypeptide; a protein; a nucleic acid; a DNA molecule; a polysaccharide; a polymer; a nanoparticle; a dendrimer.

5. A process as claimed in claim 4, wherein R" represents a heteroaryl radical or an aryl radical or an alkyl radical containing from 1 to 8 carbon atoms.

6. A process as claimed in claim 1, wherein the nitrogenous ligand is chosen from phenanthrolines, triazoles, pyridines, imidazoles and benzimidazoles.

* * * * *

UNITED STATES PATENT AND TRADEMARK OFFICE
CERTIFICATE OF CORRECTION

PATENT NO. : 9,802,980 B2
APPLICATION NO. : 14/766048
DATED : October 31, 2017
INVENTOR(S) : Frederic Taran et al.

Page 1 of 1

It is certified that error appears in the above-identified patent and that said Letters Patent is hereby corrected as shown below:

In the Claims

Column 24, Claim 1, Line 19, delete "...wherein a syndrome of formula II..." and insert --"...wherein a sydnone of formula II..."--

Signed and Sealed this
Fifteenth Day of May, 2018

Andrei Iancu
*Director of the United States Patent and Trademark Office*